US00PP21852P2

(12) United States Plant Patent
Yates

(10) Patent No.: US PP21,852 P2
(45) Date of Patent: Apr. 5, 2011

(54) *BEGONIA* PLANT NAMED 'YADEV'

(50) Latin Name: *Begonia boliviensis*
Varietal Denomination: YADEV

(76) Inventor: Frederic C. Yates, Congleton (GB)

( * ) Notice: Subject to any disclaimer, the term of this patent is extended or adjusted under 35 U.S.C. 154(b) by 0 days.

(21) Appl. No.: 12/653,014

(22) Filed: Dec. 7, 2009

(51) Int. Cl.
*A01H 5/00* (2006.01)

(52) U.S. Cl. ..... Plt./347

(58) Field of Classification Search ..... Plt./343, Plt./347, 349
See application file for complete search history.

*Primary Examiner* — Susan B McCormick Ewoldt
(74) *Attorney, Agent, or Firm* — Penny J. Aguirre

(57) ABSTRACT

A new cultivar of *Begonia boliviensis* named 'YADEV', characterized by its large single red flowers, its compact, freely branched and pendulant plant habit and its ease of propagation.

2 Drawing Sheets

Botanical classification: *Begonia boliviensis.*
Cultivar designation: 'YADEV'.

BACKGROUND OF THE INVENTION

The present invention relates to a new and distinct cultivar of *Begonia* plant, botanically known as *Begonia boliviensis* 'YADEV' and will be referred to hereafter by its cultivar name, 'YADEV'.

The new cultivar was derived from a controlled breeding program conducted by the inventor at his nursery in Congleton, Cheshire, U. K. The overall purpose of the breeding program is to make selections of *Begonia* plants with compact plant habits suitable for container use combined with superior flower performance and productive stock plants for propagation. 'YADEV' was selected in the Inventor's greenhouse in 2005 as a single unique plant from amongst the seedlings derived from a cross made between an unnamed proprietary plant of *Begonia boliviensis* as the female parent and 'YABOS' (U.S. Plant Pat. No. 20,093) as the male parent.

Asexual reproduction of the new cultivar was first accomplished by terminal stem cuttings in Congleton, Cheshire, U. K. in 2005 by the Inventor. It has been determined that the characteristics of this cultivar are stable and are reproduced true to type in successive generations.

SUMMARY OF THE INVENTION

The following traits have been repeatedly observed and represent the characteristics of the new cultivar, which in combination distinguish 'YADEV' as a new and distinct cultivar of *Begonia.*

1. 'YADEV' exhibits a compact, pendulous plant habit.
2. 'YADEV' readily produces side shoots.
3. 'YADEV' exhibits large, single red flowers.
4. 'YADEV' produces productive stock plants for propagation.

In comparison to its parents plants; the male parent, 'YABOS', differs from 'YADEV' in having smaller flowers and the female parent, an unnamed proprietary seedling, differs from 'YADEV' in having double flowers. 'YADEV' can be compared to the cultivar 'Bonfire' (U.S. Plant Pat. No. 15,108). 'Bonfire' differs from 'YADEV' in having a more upright and less pendulous plant habit and flowers that are smaller and less red in color. 'YADEV' can also be compared to cultivars from the same breeding program, which are similar in plant habit. 'Yagance' (U.S. Plant Pat. No. 19,817) differs from 'YADEV' in having bicolor pink and white flowers and 'Yamance' (U.S. Plant Pat. No. 19,777) differs from 'YADEV' in having flowers that are pink in color.

BRIEF DESCRIPTION OF THE DRAWING

The accompanying colored photographs illustrate the overall appearance and distinct characteristics of the new *Begonia*. The photographs were taken in September of a plant approximately 6 months in age as grown in a two-liter container in Swavesey, Campbridgeshire, U.K.

The photograph in FIG. 1 provides a side view of 'YADEV' in bloom.

Figure 1:
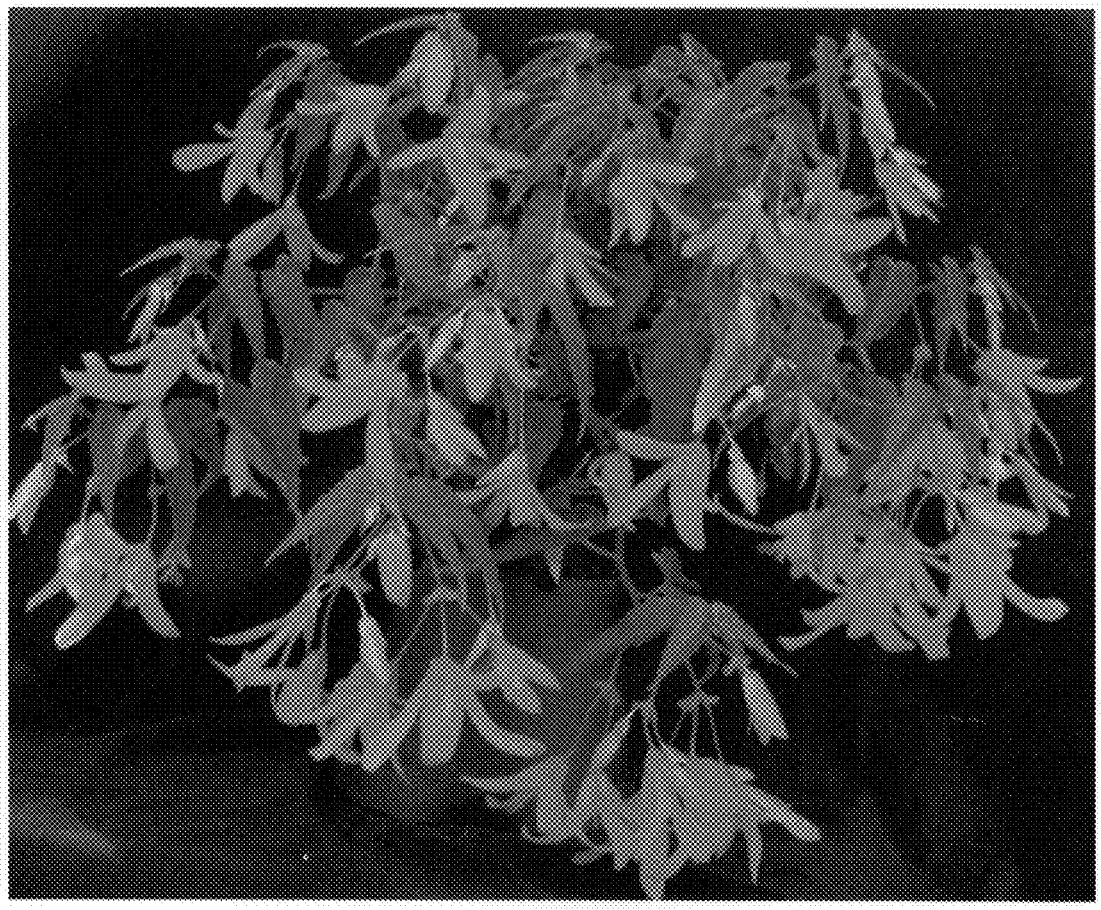
Figure 2:
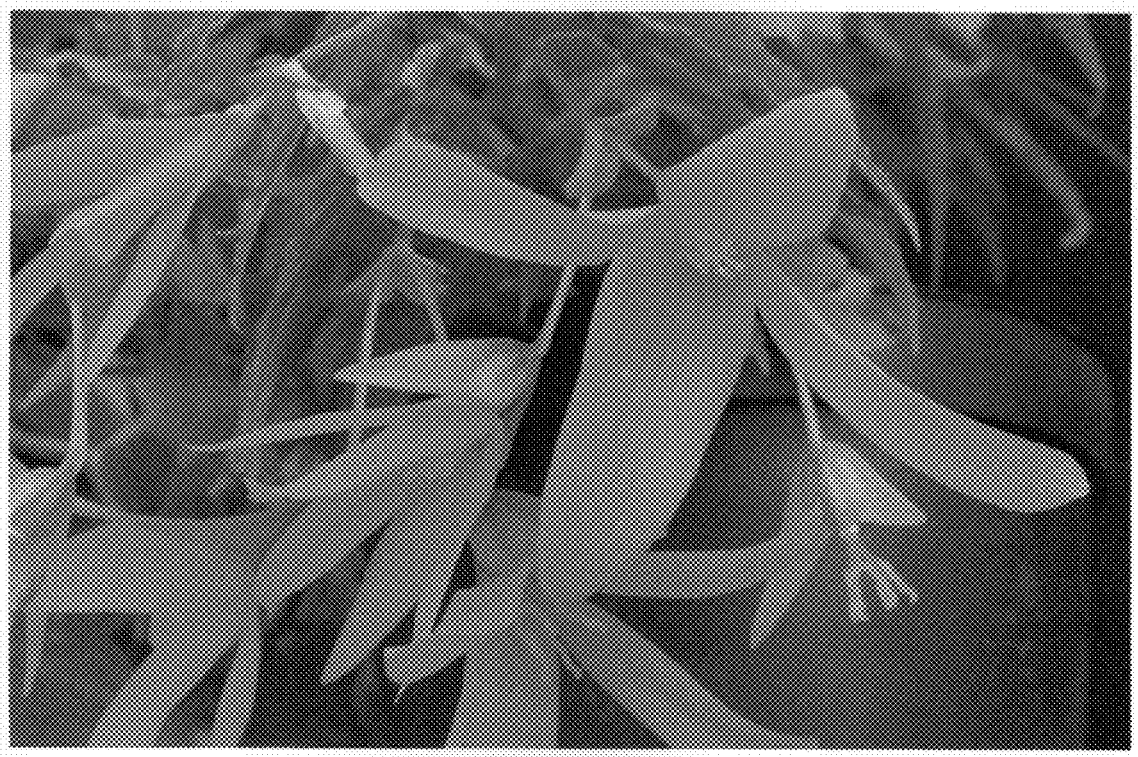

The photograph in FIG. 2 provides a close-up view of the flowers of 'YADEV'.

The colors in the photograph may differ slightly from the color values cited in the detailed botanical description, which accurately describe the colors of the new *Begonia.*

DETAILED BOTANICAL DESCRIPTION OF THE PLANT

The following is a detailed description of plants of the new cultivar approximately 6 months in age as grown in two-liter containers under greenhouse conditions with ambient light in Congleton, Cheshire, U.K. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'YADEV' is a cultivar of *Begonia boliviensis.*

Parentage: Selection from unnamed proprietary selection of *Begonia boliviensis* as the female parent and 'YABOS' as the male parent.

General plant characteristics:

*Plant type.*—Deciduous tuberous perennial, grown primarily for use in baskets and containers.

*Plant habit.*—Compact, prostrate and pendulous.

*Flowering period.*—From late March to November.

*Height and spread.*—Reaches about 26 cm in height and about 59 cm in spread.

*Cold hardiness.*—U.S.D.A. Zone 10.

*Culture.*—Grows in any commercial soil or growing media, 12 hours of light is needed for production in the winter months.

*Diseases and pests.*—No susceptibility or resistance to diseases or pests has been observed.

*Root description.*—Fleshy to fibrous with tubers produced for over-wintering.

*Tubers.*—Uneven-globose in shape and often depressed in center, an average of 8 cm in diameter (larger on older plants), surface is smooth and slightly corky, color between 199C and 199D.

Growth and propagation:

*Growth rate.*—Typical vigor for the species but with more compact growth.

*Propagation.*—Terminal stem cuttings.

*Time required for root initiation.*—10 to 14 days at 22° C.

*Time required for root development.*—5 to 8 weeks to reach commercial size.

Stem description:

*Stem size.*—Average of 31 cm in length and 1.2 cm in width with lateral branches about 5 mm in width.

*Stem shape.*—Round, solid.

*Stem color.*—176B, becoming 178A.

*Stem surface.*—Smooth, glabrous but weakly glabrous, lenticels absent.

*Internode length.*—Average of 2.7 cm.

*Branching habit.*—Freely branched.

*Branching angle at emergence.*—About 45°.

Foliage description:

*Leaf shape.*—Lanceolate, asymmetric with one side wider than the other.

*Leaf division.*—Simple.

*Leaf base.*—Rounded on narrower side, cordate on wider side.

*Leaf apex.*—Acuminate.

*Leaf venation.*—Pinnate, color 137B on upper surface and 197B on lower surface.

*Leaf margins.*—Serrate with short bristles emerging from tips of the teeth.

*Leaf attachment.*—Petiolate.

*Leaf arrangement.*—Alternate.

*Leaf surface.*—Upper surface; glabrous, smooth, lower surface; glabrous on blade and very weakly pubescent on mid vein.

*Leaf color.*—Upper surface; 137A, lower surface; 137D.

*Leaf size.*—Average of 9 cm in length and 3.2 cm in width.

*Leaf quantity.*—Average of 14 per branch.

*Leaf fragrance.*—None.

*Petioles.*—About 1.8 cm in length and 2 mm in width, surface is very sparsely pubescent with simple hairs, color is 176C.

*Stipules.*—Ovate-triangular in shape, 181C in color and rapidly becoming dry and papery, about 6 mm in length and 4 mm in width.

Flower description:

*Inflorescence type.*—2 to 3 flowered cyme produced sequentially in the axils of the upper leaves, monoecious with terminal male flowers developing before the lateral female flowers.

*Peduncles.*—About 3.3 cm in length and 2 mm in width, 179A in color, pubescence is absent.

*Flower persistence.*—Self-cleaning.

*Flower type.*—Single, rotate, un-fused tepals.

*Flower fragrance.*—None.

*Flower number.*—Average of 10 per inflorescence, one inflorescence per stem.

*Flower aspect.*—Hanging.

*Bracts.*—2, present at base of cyme, round in shape, acute bifid apex, about 1 cm in length and 1.2 cm width, 180B in color.

Male flowers:

*Pedicels.*—About 2.7 cm in length and 2 mm in width, 40A in color, glabrous surface.

*Flower buds.*—Flattened ovoid in shape, about 3.2 cm in length and 1.5 cm in width, 42A in color.

*Flower size.*—About 5.5 cm in length and 7 cm in width.

*Tepals.*—4 in number (2 inner and 2 outer), outer tepals; ovate in shape, recurved near the apex, obtuse apex, rounded base, average of 5.8 cm in length and 2.5 cm in width, glabrous and smooth surface, entire margin, inner surface 40A in color, outer surface 41A in color.

*Corolla form.*—Spreading, tepals are un fused.

*Stamens.*—Numerous, connate below forming a tube, about 2.8 cm in length and 1 mm in width, 163B in color.

*Filaments.*—About 3 mm in length and 0.5 mm in width, 163B in color.

*Anthers.*—Broadly elliptic in shape, about 1 mm in length and <1 mm in width, 163A in color.

*Pollen.*—Copious in quantity, 8C in color.

Female flowers:

*Pedicels.*—About 3.4 cm in length and 1.5 mm in width, 40A in color, glabrous surface.

*Flower buds.*—Flattened ovoid in shape, about 2.4 cm in length and 9 mm in width, 42A in color.

*Flower size.*—About 4 cm in length and 4.7 cm in width.

*Tepals.*—5 in number (3 inner and 2 outer), outer tepals; ovate in shape, acute apex, rounded base, average of 4.2 cm in length and 1.5 cm in width, glabrous and smooth surface, entire margin, inner and outer surface 40A in color, inner tepals; linear-elliptic in shape, recurved near the apex, acute apex, narrowly cuneate base, average of 4.2 cm in length and 9 mm in width, glabrous and smooth surface, entire margin, inner and outer surface 40A in color.

*Corolla form.*—Spreading, tetals are un-fused.

*Styles.*—3 in number, cylindrical, connate for basal 1 mm, about 5 mm in length and <1 mm in width, 40A in color.

*Stigmas.*—Bifid in shape, lobes about 8 mm in length and <1 mm in width, 17B in color.

*Ovaries.*—Inferior, about 1.1 cm in length and 9 mm in width (excluding wings), color is 175D merging to 44B at tips of the wings.

*Seed.*—Very numerous, ovate-elliptic in shape, N167B in color, extremely small in size.

It is claimed:

1. A new and distinct cultivar of *Begonia* plant named 'YADEV' as herein illustrated and described.

* * * * *